United States Patent
Prasit et al.

(12)

(10) Patent No.: US 6,329,421 B1
(45) Date of Patent: Dec. 11, 2001

(54) DIARYL BICYCLIC HETEROCYCLES AS INHIBITORS OF CYCLOOXYGENASE-2

(75) Inventors: Petpiboon Prasit; Daniel Guay; Zhaoyin Wang; Serge Leger; Michel Therien, all of Kirkland (CA)

(73) Assignee: Merck Frosst Canada & Co., Quebec (CA)

( * ) Notice: Subject to any disclaimer, the term of this patent is extended or adjusted under 35 U.S.C. 154(b) by 1130 days.

(21) Appl. No.: 08/793,931

(22) PCT Filed: Aug. 24, 1995

(86) PCT No.: PCT/CA95/00490

§ 371 Date: Feb. 25, 1997

§ 102(e) Date: Feb. 25, 1997

(87) PCT Pub. No.: WO96/06840

PCT Pub. Date: Mar. 7, 1996

Related U.S. Application Data

(63) Continuation of application No. 08/297,461, filed on Aug. 29, 1994, now Pat. No. 5,521,213.

(51) Int. Cl.$^7$ ............... A61K 31/34; A61K 31/38; C07D 307/80; C07D 333/56
(52) U.S. Cl. ............... 514/443; 514/469; 544/238; 544/376; 548/125; 548/127; 548/128; 548/131; 548/134; 548/136; 548/143; 548/159; 548/235; 548/247; 549/6; 549/220; 549/51; 549/57; 549/58; 549/469
(58) Field of Search ............ 549/58, 469; 514/443, 514/469

(56) References Cited

U.S. PATENT DOCUMENTS 4,477,463  10/1984  Cherkofsky ................ 548/560
4,652,582  3/1987  Wilkerson ................... 514/427
4,767,766  8/1988  Baker et al. ................. 514/301

FOREIGN PATENT DOCUMENTS

WO 94/15932  7/1994  (WO).
WO 94/26731  11/1994  (WO).

OTHER PUBLICATIONS

Wilkerson, et al., Journal of Medicinal Chemistry, vol. 37, No. 7, pp. 988–998 (1994).
Effenberger, et al., Chem. Ber. vol. 115, No. 12, pp. 3719–3736 (1982).
Chem. Abstracts, vol. 44, Ab. No. 2510b.
Chem. Abstracts, vol. 113, No. 22, Ab. No. 201340m CA.
Valadovska, et al., CA, vol. 102, Ab. No. 29329 (1984).
Ivanov, et al., CA, vol. 70, Ab. No. 3595 (1966).

*Primary Examiner*—Bernard Dentz
(74) *Attorney, Agent, or Firm*—Curtis C. Panzer; David L. Rose

(57) ABSTRACT

The invention encompasses the novel compound of Formula I as well as a method of treating cyclooxygenase-2 mediated diseases comprising administration to a patient in need of such treatment of a non-toxic therapeutically effective amount of a compound of Formula I.

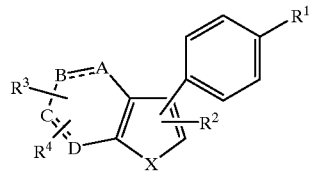

The invention also encompasses certain pharmaceutical compositions for treatment of cyclooxygenase-2 mediated diseases comprising compounds of Formula I.

17 Claims, No Drawings

DIARYL BICYCLIC HETEROCYCLES AS INHIBITORS OF CYCLOOXYGENASE-2

RELATED APPLICATION DATA

This is a National application of PCT/CA95/00490, filed Aug. 24, 1995, which is a continuation of U.S. Ser. No. 08/297,461, filed Aug. 29, 1994, which has now issued as U.S. Pat. No. 5,521,213 on May 28, 1996.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 or the constitutive enzyme, as originally identified in bovine seminal vesicles. More recently the gene for a second inducible form of cyclooxygenase (cyclooxygenase-2) has been cloned, sequenced and characterized initially from chicken, murine and human sources. This enzyme is distinct from the cyclooxygenase-1 which has been cloned, sequenced and characterized from various sources including the sheep, the mouse and man. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

A brief description of the potential utility of cyclooxygenase-2 inhibitors is given in an article by John Vane, *Nature*, Vol. 367, pp. 215–216, 1994.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

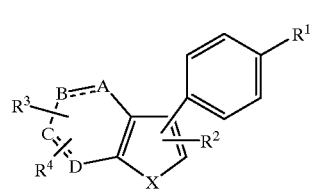

The invention also encompasses certain pharmaceutical compositions for treatment of cyclooxygenase-2 mediated diseases comprising compounds of Formula I.

DETAILED DESCRIPTION OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

and pharmaceutically acceptable salts thereof wherein:
—A=B—C=D— is selected from the group consisting of:
(a) —CH=CH—CH=CH—,
(b) —$CH_2$—$CH_2$—$CH_2$—C(O)—, —$CH_2$—$CH_2$—C(O)—$CH_2$—, —$CH_2$—C(O)—$CH_2$—$CH_2$—, —C(O)—$CH_2$—$CH_2$—$CH_2$—,
(c) —$CH_2$—$CH_2$—C(O)—, —$CH_2$—C(O)—$CH_2$—, —C(O)—$CH_2$—$CH_2$—
(d) —$CH_2$—$CH_2$—O—C(O)—, $CH_2$—O—C(O)—$CH_2$—, —O—C(O)—$CH_2$—$CH_2$—,
(e) —$CH_2$—$CH_2$—C(O)—O—, —$CH_2$—C(O)—$OCH_2$—, —C(O)—O—$CH_2$—$CH_2$—,
(f) —C($R^7$)$_2$—O—C(O)—, —C(O)—O—C($R^7$)$_2$—, —O—C(O)—C($R^7$)$_2$—, —C($R^7$)$_2$—C(O)—O—,
(g) —N=CH—CH=CH—,
(h) —CH=N—CH=CH—,
(i) —CH=CH—N=CH—,
(j) —CH=CH—CH=N—,
(k) —N=CH—CH=N—,
(l) —N=CH—N=CH—,
(m) —CH=N—CH=N—,
(n) —S—CH=N—,
(o) —S—N=CH—,
(p) —N=N—NH—,
(q) —CH=N—S—,
(r) —N=CH—S—, $R^1$ is selected from the group consisting of
(a) S(O)$_2$$CH_3$,
(b) S(O)$_2$$NH_2$,
(c) S(O)$_2$$NHCOCF_3$,
(d) S(O)(NH)$CH_3$,
(e) S(O)(NH)$NH_2$,
(f) S(O)(NH)$NHCOCF_3$,
(g) P(O)($CH_3$)OH, and
(h) P(O)($CH_3$)$NH_2$, $R^2$ is selected from the group consisting of
(a) $C_{1-6}$alkyl,
(b) $C_{3-7}$ cycloalkyl,
(c) mono- or di-substituted phenyl or naphthyl wherein the substituent is selected from the group consisting of
(1) hydrogen,
(2) halo, including F, Cl, Br, I,
(3) $C_{1-6}$alkoxy,
(4) $C_{1-6}$alkylthio,
(5) CN,
(6) $CF_3$,
(7) $C_{1-6}$alkyl,
(8) $N_3$,
(9) —$CO_2H$,
(10) —$CO_2$—$C_{1-4}$alkyl,
(11) —$C(R^5)(R^6)$—OH,
(12) —$C(R^5)(R^6)$—O—$C_{1-4}$alkyl, and
(13) —$C_{1-6}$alkyl-$CO_2$—$R^8$;
(d) mono- or di-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, 3, or 4 additional N atoms; said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl;
(e) benzoheteroaryl which includes the benzo fused analogs of (d);
$R^3$ and $R^4$ are the substituents residing on any position of —A=B—C=D— and are selected independently from the group consisting of:
(a) hydrogen,
(b) $CF_3$,
(c) CN,
(d) $C_{1-6}$alkyl,
(e) —$Q^1$ wherein $Q^1$ is $Q^2$, $CO_2H$, $C(R^5)(R^6)OH$,
(f) —O—$Q^2$,
(g) —S—$Q^2$, and
(h) optionally substituted
(1) —$C_{1-5}$alkyl-$Q^1$,
(2) —O—$C_{1-5}$alkyl-$Q^1$,
(3) —S—$C_{1-5}$alkyl-$Q^1$,
(4) —$C_{1-3}$alkyl-O—$C_{1-3}$alkyl-$Q^1$,
(5) —$C_{1-3}$alkyl-S—$C_{1-3}$alkyl-$Q^1$,
(6) —$C_{1-5}$alkyl-O—$Q^2$,
(7) —$C_{1-5}$alkyl-S—$Q^2$,
wherein the substituent resides on the alkyl chain and the substituent is $C_{1-3}$alkyl, and $Q^1$ is $Q^2$, $CO_2H$, $C(R^5)(R^6)OH$ $Q^2$ is $CO_2$—$C_{1-4}$alkyl, tetrazolyl-5-yl, or $C(R^5)(R^6)O$—$C_{1-4}$alkyl; $R^5$, $R^6$ and $R^7$ are each independently selected from the group consisting of
(a) hydrogen,
(b) $C_{1-6}$alkyl,
or $R^5$ and $R^6$ together with the carbon to which they are attached form a saturated monocyclic carbon ring of 3, 4, 5, 6 or 7 atoms, or two $R^7$ groups on the same carbon form a saturated monocyclic carbon ring of 3, 4, 5, 6 or 7 atoms;

$R^8$ is hydrogen or $C_{1-6}$alkyl.
$R^9$ is hydrogen, $C_{1-6}$alkyl or aryl.
X is O, S, $NR^9$, CO, $C(R^9)_2$, $C(R^9)(OH)$, —$C(R^9)$=C$(R^9)$—; —$C(R^9)$=N—;
—N=$C(R^9)$—.
Exemplifying the invention are:
(a) 3-(4-(Methylsulfonyl)phenyl)-2-phenylbenzo[b]furan
(b) 3-(4-(Methylsulfonyl)phenyl)-2-phenylbenzo[b]-thiophene
(c) 3-(4-(Methylsulfonyl)phenyl)-2-phenyl-inden-1-one
(d) 2-(4-Fluorophenyl)-3-(4-(methylsulfonyl)-phenyl)indole
(e) 3-(4-Fluorophenyl)-2-(4-(methylsulfonyl)phenyl)indole
(f) 2-(4-Fluorophenyl)-3-(4-(methylsulfonyl)phenyl)-4H-thieno[2,3-c]furan-6-one
(g) 2-(3,4-Difluorophenyl)-3-(4-(methylsulfonyl)-phenyl)4H-thieno[2,3-c]furan-6-one
(h) 2-(4-Fluorophenyl)-3-(4-(aminosulfonyl)phenyl)-4H-thieno[2,3-c]furan-6-one
(i) 2-(3,4-Difluorophenyl)-3-(4-(aminosulfonyl)phenyl)-4H-thieno[2,3-c]furan-6-one
(j) 2-Phenyl-3-(4-(methylsulfonyl)phenyl)4,7-dihydro-thieno[2,3-c]pyran-5-one
The following abbreviations have the indicated meanings:
Ac=acetyl
C.I.=chemical ionization
DBU=1,8-diazabicyclo[5.4.0]undec-7-ene
DMF=N,N-dimethylformamide
DMSO=dimethyl sulfoxide
DMAP=4-dimethylaminopyridine
MMPP=monoperoxyphthalic acid??
MMPP=magnesium monoperoxyphthalate
MPPM=monoperoxyphthalic acid, magnesium salt hexahydrate
NBS=N-bromosuccinimide
NSAID=non-steroidal anti-inflammatory drug
PCC=Pyridinium chlorochromate
PDC=pyridinium dichromate
Ph=phenyl
PPA=polyphosphoric acid
r.t.=room temperature
Swern's=DMSO+oxalyl chloride
TFAA=trifluoroacetic anhydride
THF=tetrahydrofuran
TLC=thin layer chromatography
Alkyl group abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Alkyl refers to linear or branched structures and combinations thereof.

Halo includes F, Cl, Br, and I.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like, and basic ion exchange resins.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma, Alzheimer's Disease and osteoporosis.

By virtue of its high cyclooxygenase-2 (COX-2) activity and/or its specificity for cyclooxygenase-2 over cyclooxygenase-1 (COX-1), compound I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudoephedrine, oxymetazoline, epinephrine, naphazoline, xylometazoline, propylhexedrine, or levodesoxyephedrine; an antiitussive including codeine, hydrocodone, caramiphen, carbetapentane, or dextromethorphan; a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methycellulose, hydroxy-propylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods.

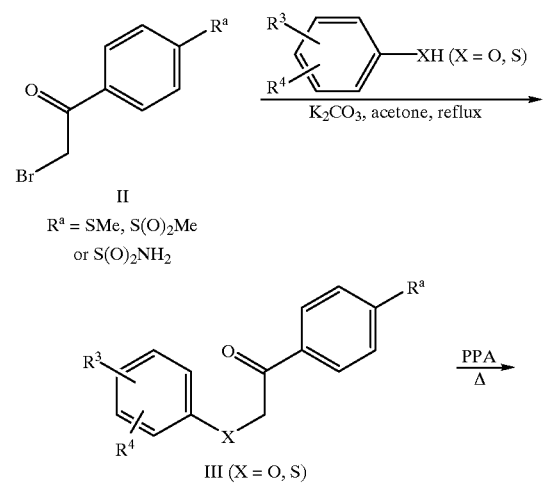

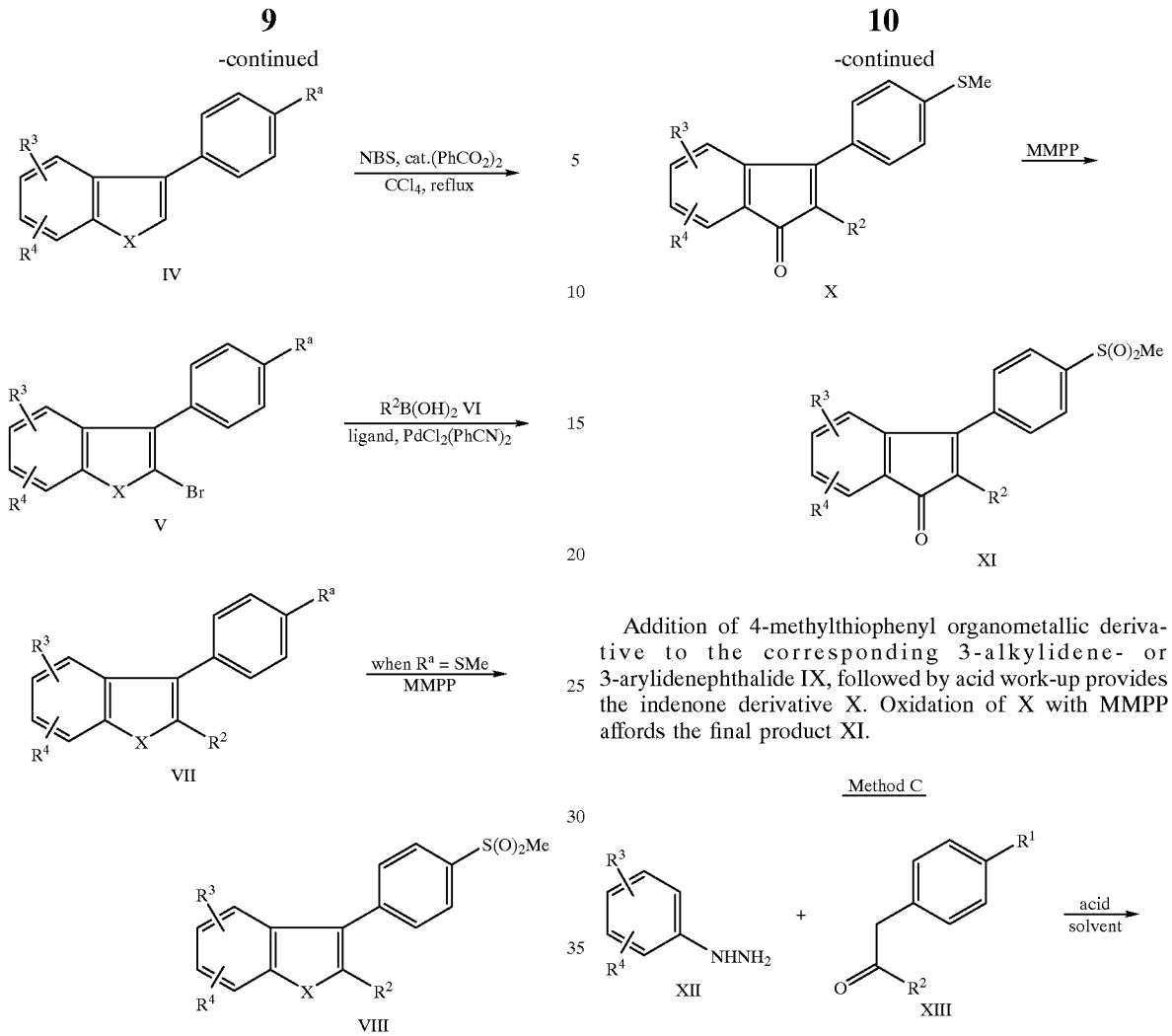

Alkylation of a phenol or thiophenol with 4'-substituted 2-bromoacetophenone II in the presence of a base such as $K_2CO_3$ affords ketone III, which can be cyclized to a benzofuran or benzothiophene derivative IV by treatment with a dehydrating agent such as PPA. Bromination of IV with bromine or NBS provides a 2-brominated product V. Cross-coupling of V with a alkyl or aryl boric acid VI can be effected by catalysis with Pd to give the desired product VII. When $R^a$ is SMe in the starting material II an oxidation of VII with MMPP or similar reagent will furnish the final product. It will be evident to one skilled in the art that the substituents $R^3$ and $R^4$ must be compatible with the chemistry described in this method.

Addition of 4-methylthiophenyl organometallic derivative to the corresponding 3-alkylidene- or 3-arylidenephthalide IX, followed by acid work-up provides the indenone derivative X. Oxidation of X with MMPP affords the final product XI.

A solution of the hydrazine XII and the ketone XIII in an inert solvent such as CH$_2$Cl$_2$, toluene or acetic acid is stirred at room or elevated temperature in the presence of an acid catalyst such as CH$_3$SO$_3$H, H$_2$SO$_4$, P$_2$O$_5$, etc., until the reaction is complete. The resultant indoles can be isolated by standard workup. Purification is usually accomplished by chromatography on silica gel or crystallization from the appropriate solvents. Similarly, ketone XIIIa gives rise to product XIVa.

such as PDC, PCC, MnO$_2$ or Swern's reagent. A peracid derivative can be used to convert XVIII to methyl sulphone XIX, which is converted to thiophene XX upon treatment with methyl thioglycolate and a base, such as a tertiary amine. Benzylic bromination of XX with NBS provides bromide XXI. Treatment of XXI with n-Bu$_4$NOAc followed an alkali hydroxide in an aqueous solvent results in hydrolysis of the methyl ester group and conversion of the bromide

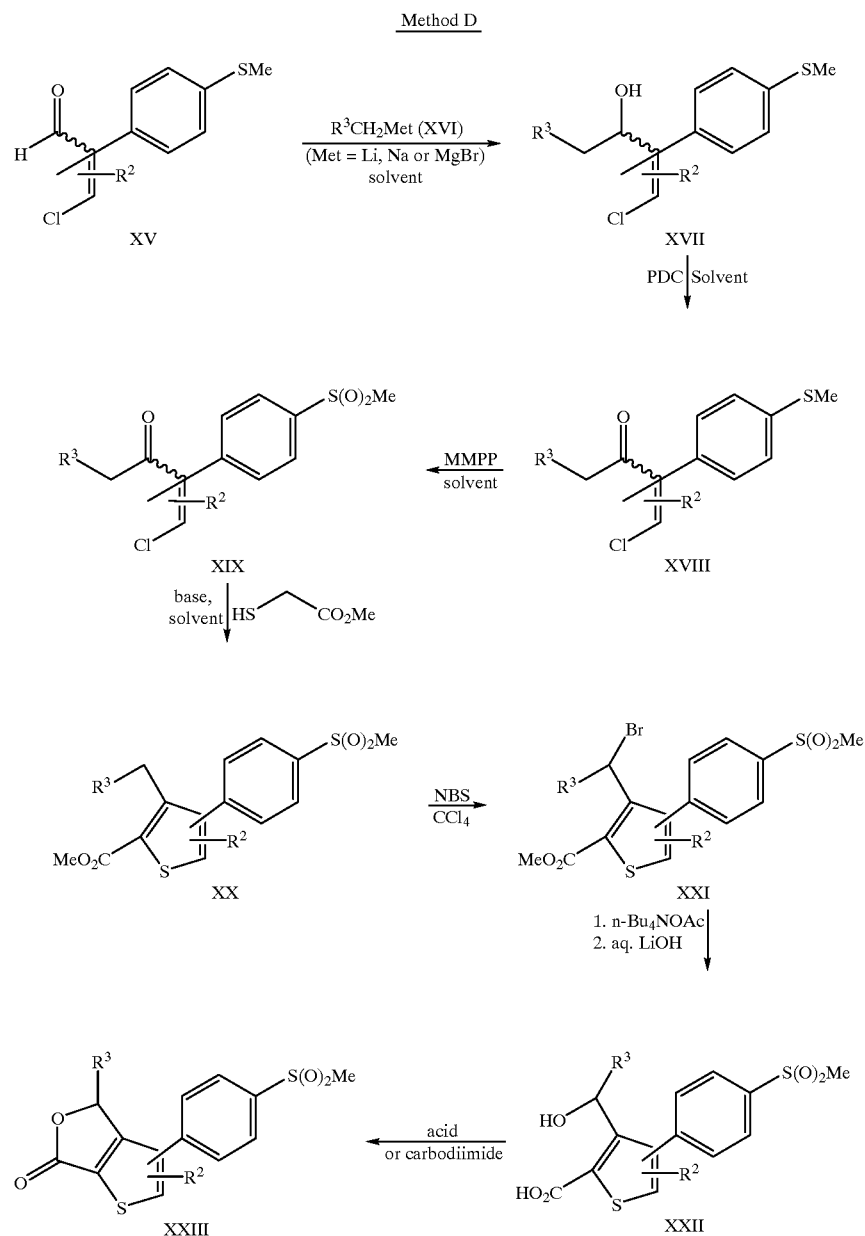

Method D

Reaction of the readily available aldehyde XV with an organometallic reagent XVI provides allylic alcohol XVII, which can be oxidized to ketone XVIII by an oxidizing agent group to hydroxy to yield the desired hydroxy acid XXII, which can be converted to its closed form XXIII upon treatment with an acid or a dehydrating agent, such as a carbodiimide.

Method E

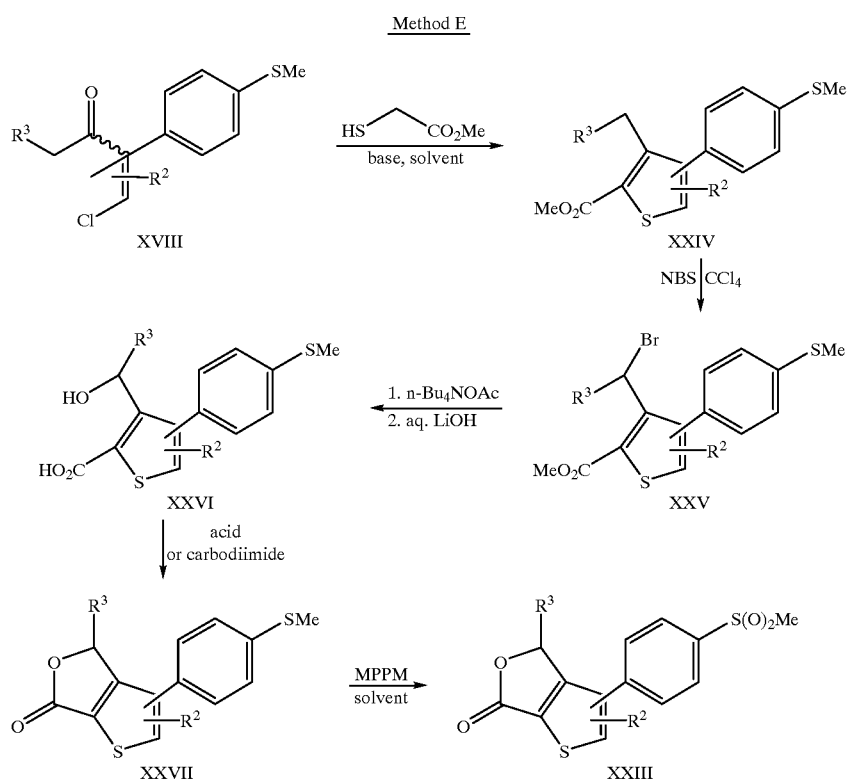

The difference between Method D and Method E is that the methylsulfonyl group is introduced at the end of the synthetic sequence in E. Reaction of XVIII with methyl thioglycolate and a base, such as a tertiary amine, provides thiophene XXIV. Following the same sequence as described in Method D, XXIV could be transformed to thiophene derivative XXVII. Oxidation of XXVII with peracid provides the desired compound XXIII.

Method F

Oxidation of XXVII with one equivalent of peracid followed by treatment of the resulting sulfoxide with TFAA at reflux affords compound XXVIII. The desired sulfonamide XXIX can then be formed by the method of Kharash (*J. Am. Chem. Soc.*, 1951, 73, 3240).

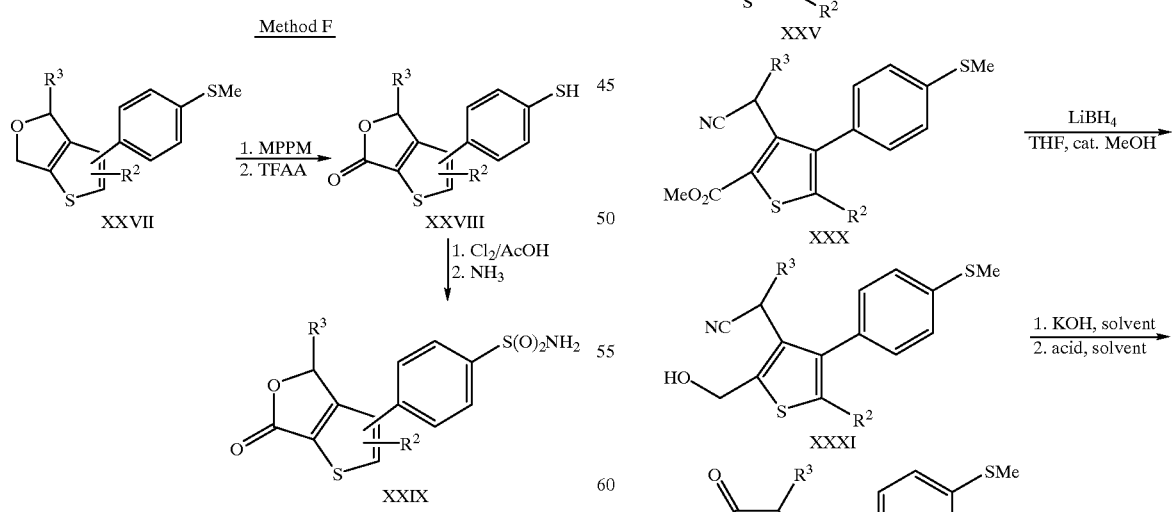

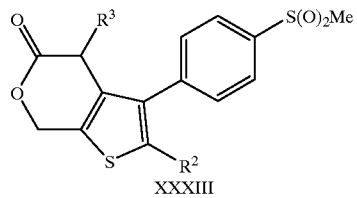

XXXIII

Reaction of XXV with NaCN in a polar solvent affords nitrile XXX. Reduction of XXX with LiBH₄ yields alcohol XXXI, which can be hydrolyzed by a base and cyclized by an acid to provide lactone XXXII. The final product XXXIII is obtained by oxidation of XXXII with MPPM.

Representative Compounds

Table I and II illustrate compounds of Formula I, which are representative of the present invention.

TABLE I

| | Example | Method |
|---|---|---|
| 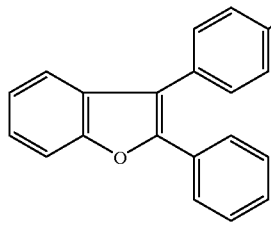 | 1 | A |
| 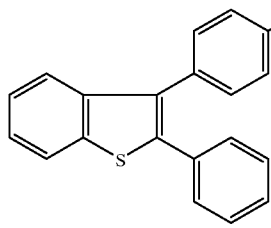 | 2 | A |
| 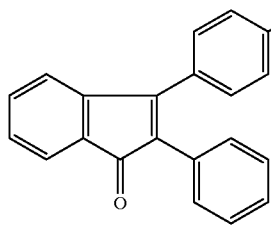 | 3 | B |
| 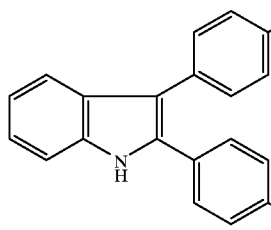 | 4 | C |

TABLE I-continued

| | Example | Method |
|---|---|---|
| 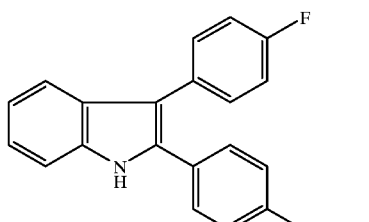 | 5 | C |
| 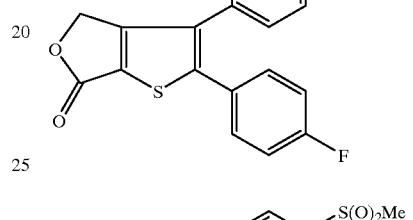 | 6 | D |
| 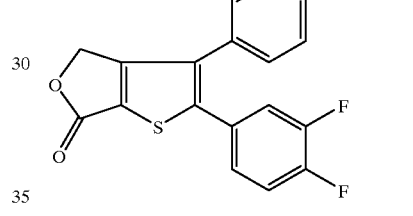 | 7 | E |
| 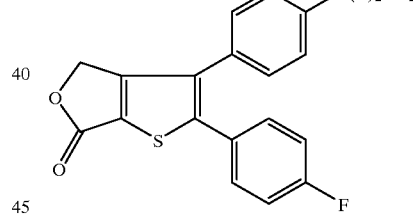 | 8 | F |
| 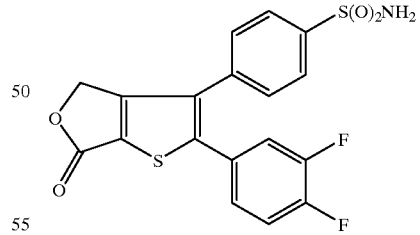 | 9 | F |
| 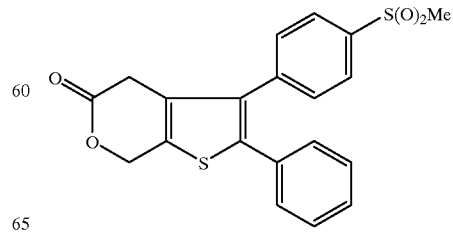 | 10 | G |

TABLE I-continued
| | Example | Method |
|---|---|---|
| (structure) | 11 | E |
TABLE II
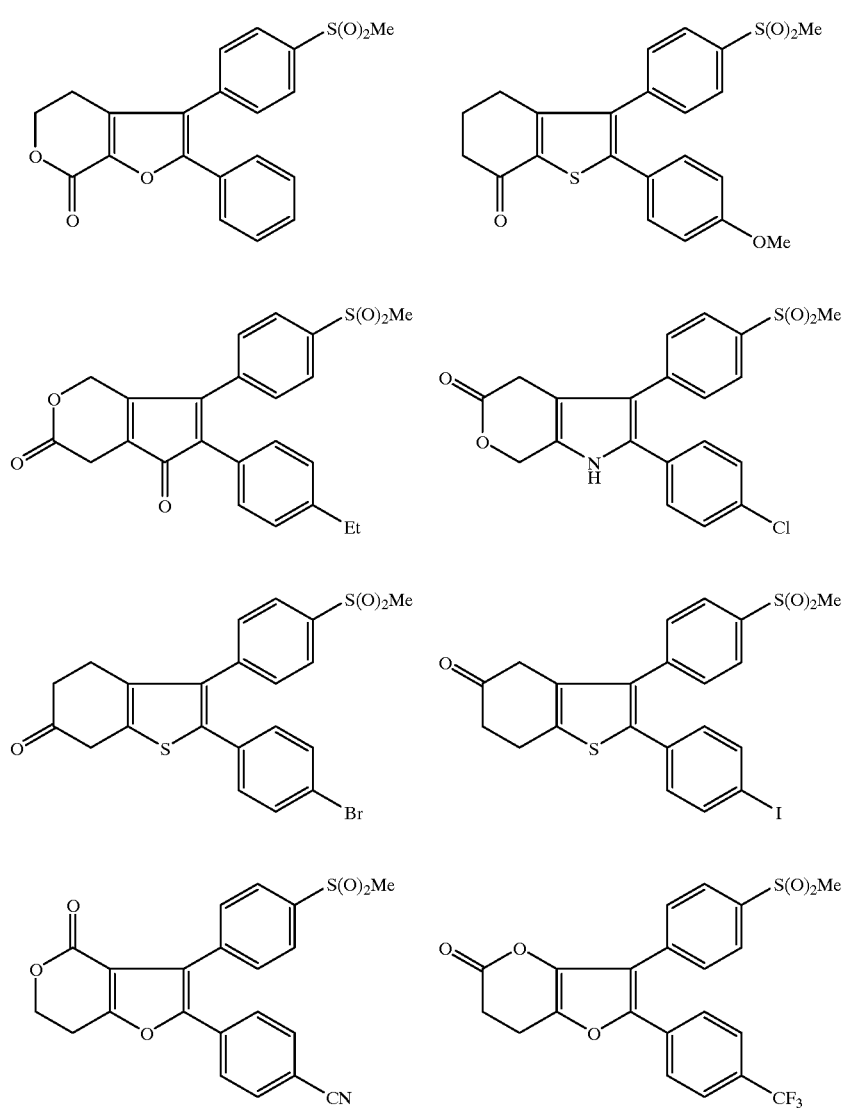

TABLE II-continued
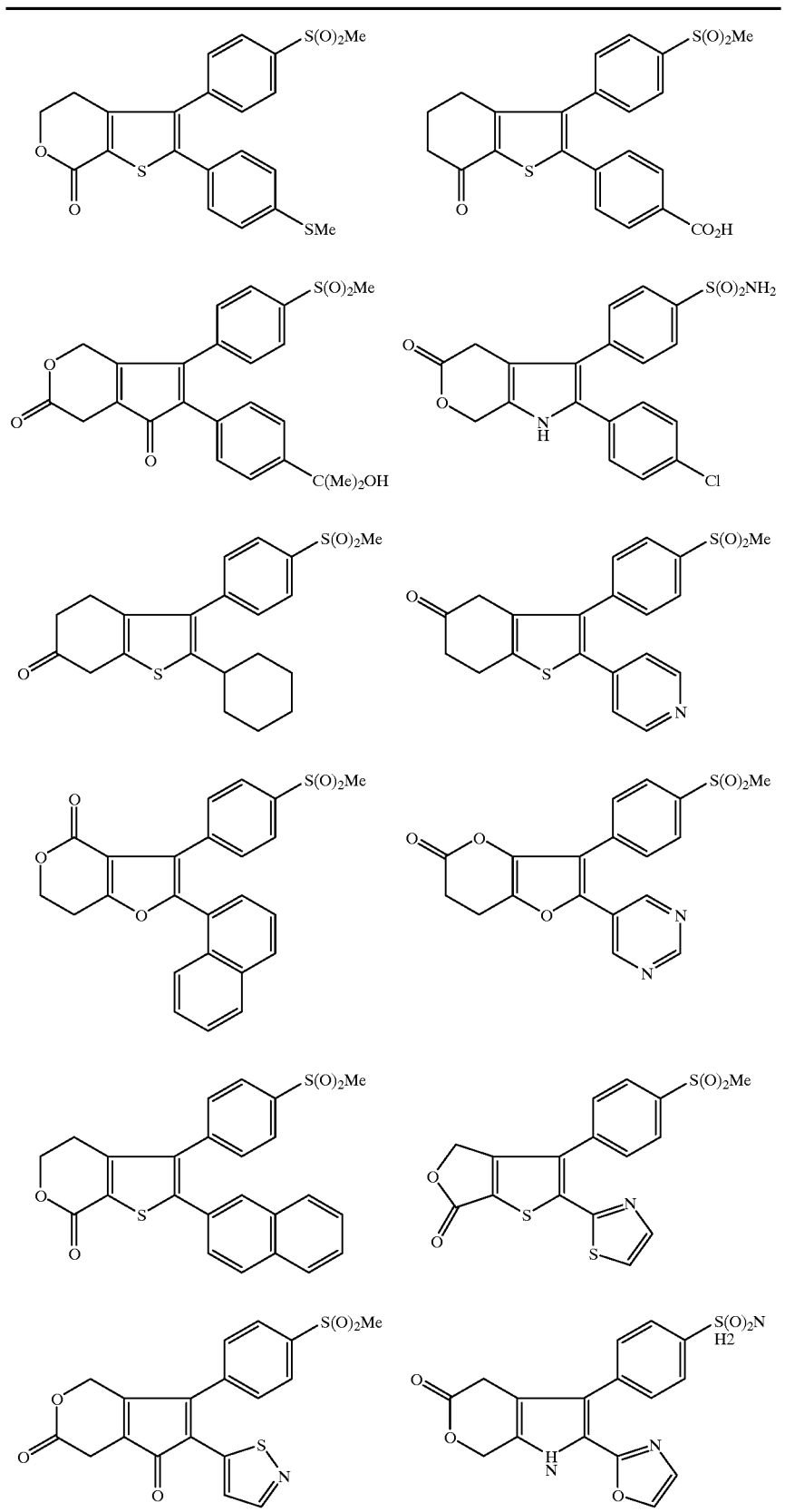

TABLE II-continued
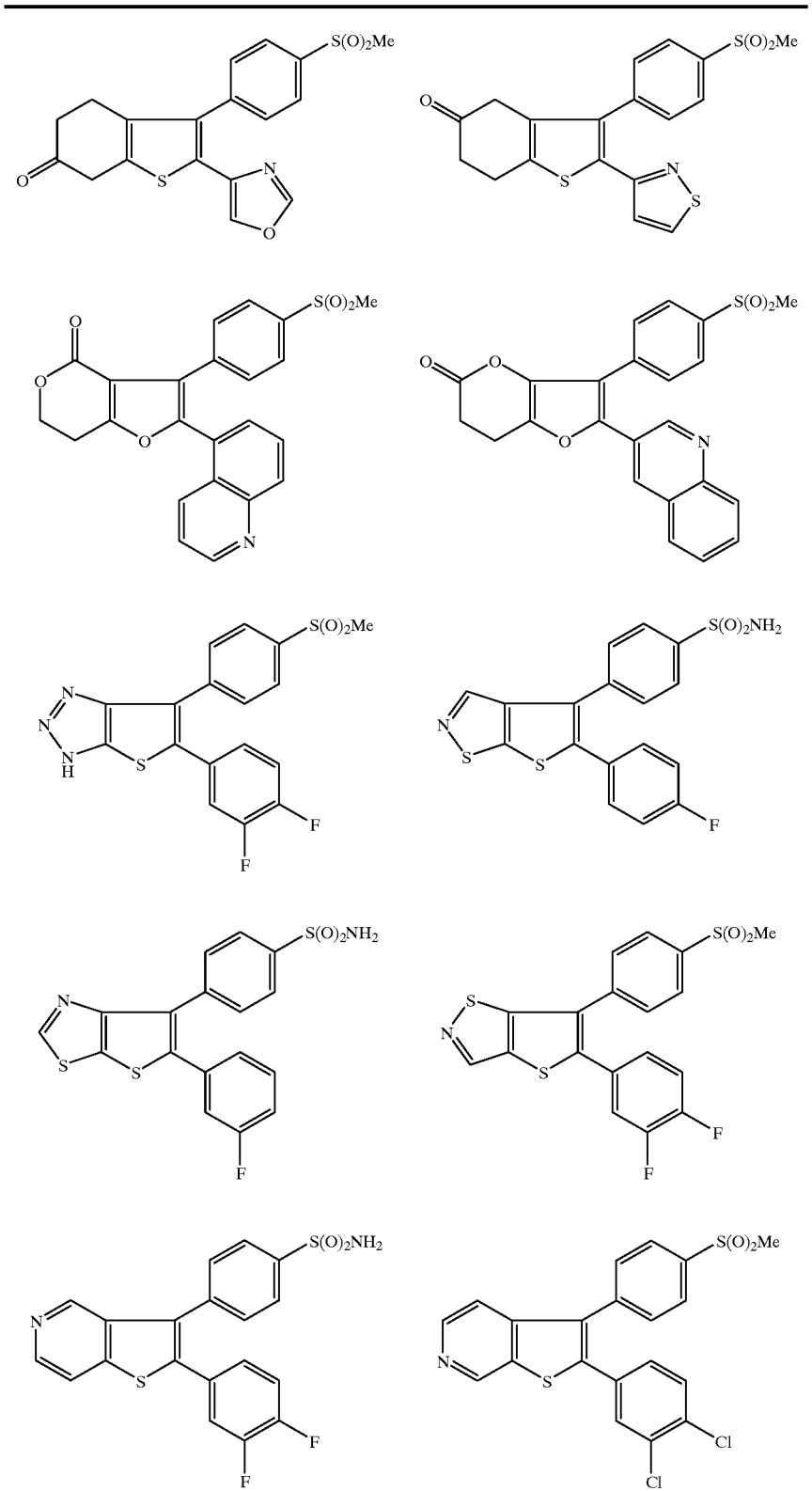

TABLE II-continued

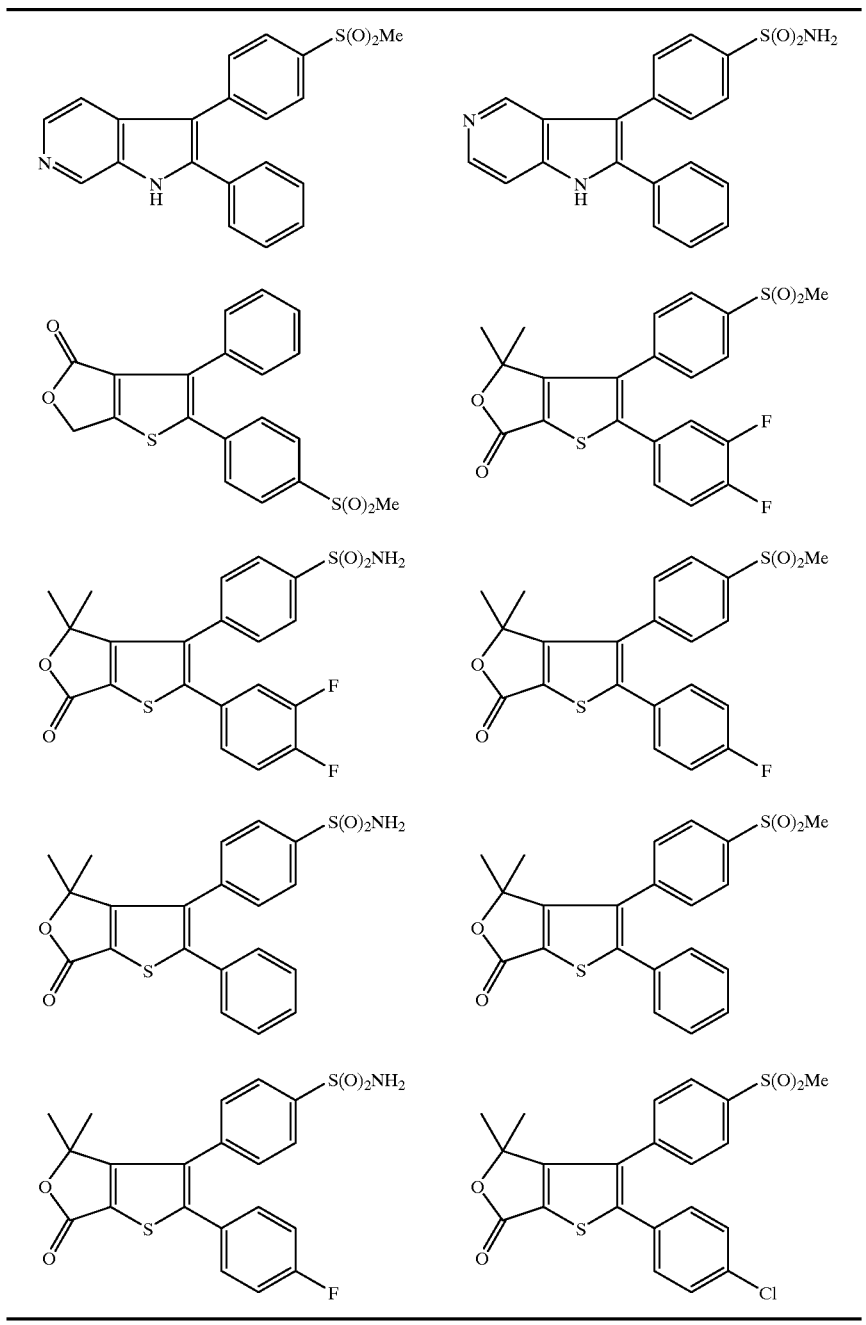

The compound of Formula I can be tested using the following assays to determine their cyclooxygenase-2 inhibiting and antiinflammatory activities.

Inhibition of Cyclooxygenase Activity

Compounds were tested as inhibitors of cyclooxygenase activity in whole cell and microsomal cyclooxygenase assays. Both of these assays measured prostaglandin $E_2$ synthesis in response to arachidonic acid, using a radioimmunoassay. Cells used for whole cell assays, and from which microsomes were prepared for microsomal assays, were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition.

Rat Paw Edema Assay—Protocol

Male Sprague-Dawley rats (150–200 g) were fasted overnight and were given p.o. either vehicle (1% methocel) or a test compound. One hr later, a line was drawn using a permanent marker at the level above the ankle in one hind paw to define the area of the paw to be monitored. The paw volume ($V_0$) was measured using a plethysmometer (Ugo-Basile, Italy) based on the principle of water displacement. The animals were then injected subplantarly with 50 μl of 1% carrageenan solution in saline (FMC Corp, Maine) into the paw using an insulin syringe with a 25-gauge needle (i.e.

500 μg carrageenan per paw). Three hr later, the paw volume ($V_3$) was measured and the increases in paw volume ($V_3-V_0$) were calculated. The animals were sacrificed by $CO_2$ asphyxiation and the absence or presence of stomach lesions scored. Data were compared with the vehicle-control values and percent inhibition calculated. Since a maximum of 60–70% inhibition (paw edema) was obtained with standard NSAIDs, $ED_{30}$ values were used for comparison. All treatment groups were coded to eliminate observer bias.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control. For purposes of this specification, a compound is a selective inhibitor of COX-2 over COX-1 if the ratio of $IC_{50}$'s for COX-1: COX-2 is 100 or greater, preferably 500 or greater.

The results for inhibition of $PGE_2$ production may be seen in Table III.

TABLE III

| Example | Conc. (nM) | Cox-2% inhib. | Cox-1% inhib. |
|---|---|---|---|
| 1 | 100 | 94 | 0 |
| 2 | 1000 | 17 | 3 |
| 3 | 100 | 80 | 5 |
| 4 | 10 | 58 | nd* |
| 4 | 1000 | nd | 0 |
| 5 | 100 | 86 | 21 |
| 6 | 15 | 50 | 0 |
| 7 | 100 | 64 | nd |
| 7 | 1000 | 100 | 4 |
| 8 | 100 | 42 | nd |
| 8 | 10000 | nd | 26 |
| 9 | 100 | 98 | nd |
| 9 | 1000 | 99 | 21 |
| 10 | 100 | 65 | nd |
| 10 | 1000 | 91 | 28 |

*nd = not done

The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm. Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta ($\delta$) values for major diagnostic protons, given in parts per million (ppm) relative to tetramethylsilane (TMS), determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliter(s)), g (gram (s)), mg (milligram(s)), mol (mole)s)), mmol (millimole(s)), eq (equivalent(s)). (Add others as necessary.)

EXAMPLE 1

3-(4-(Methylsulfonyl)phenyl)-2-phenylbenzo[b]furan

Step 1: 2-phenoxy-1-(4-(methylthio)phenyl)ethanone

To a solution of phenol (9.4 g) and 2-bromo-1-(4-(methylthio)phenyl)ethanone (12.5 g) in 500 mL of acetone was added $K_2CO_3$ (13.8 g). The mixture was refluxed for 12 h, then diluted with 500 mL of 1:1 hexane/EtOAc. The solid was removed by filtration and the filtrate was concentrated. The residue was dissolved in $Et_2O$ (500 mL), washed with 1N NaOH (100 ml) and dried over $MgSO_4$. After filtration and concentration, the title compound (9 g) was collected by filtration and air dried.

Step 2: 3-(4-(Methythio)phenyl)-benzo[b]furan

A mixture of the product of Step 1 (7 g) and PPA (50 g) was heated for 2 h at 70° C., and then cooled in ice-water bath. Ice-water (100 mL) was added slowly and the mixture was extracted with $Et_2O$ (500 mL). The extract was dried over $MgSO_4$ and concentrated to give the title compound (1.7 g).

Step 3: 2-Bromo-3-(4-(methylthio)phenyl)benzo[b]furan

A solution of the product of Step 2 (100 mg), NBS (90 mg) and benzoyl peroxide in $CCl_4$ (5 mL) was heated to reflux under a spotlight for 30 min. The mixture was cooled, diluted with $Et_2O$ (3 ml) and filtered. The filtrate was concentrated and the residue was purified by flash chromatrography, eluted with 15:1 hexane/EtOAc to give the title compound (120 mg).

Step 4: 3-(4-(Methylthio)phenyl)-2-phenylbenzo[b]furan

A mixture of the product of Step 3 (450 mg), phenylboric acid (750 mg), Pd $(PPh_3)_4$ (80 mg) and NaOH (3 mL, 1N) in toluene (8 ml) and EtOH (10 mL) was refluxed for 20 h. A saturated solution of $NaHCO_3$ (50 ml) was added and the mixture was extracted with $Et_2O$ (200 mL). The extract was dried over $MgSO_4$ and concentrated. The residue was purified by flash chromatography eluted with 30:1 hexane/EtOAc to give the title compound (300 mg).

Step 5: 3-(4-(Methanesulfonyl)phenyl)-2-phenylbenzo[b]furan

To a solution of the product of Step 4 (300 mg) in 25 mL of 10:1 $CH_2Cl_2$/MeOH was added 500 mg of MMPP. The mixture was stirred for 2 h and then diluted with 25 mL of EtOAc. The solid was removed by filtration and the filtrate was concentrated. The residue was purified by flash chromatography eluted with 3:1 hexane/EtOAc to give the title compound (250 mg).

$^1$H NMR (acetone-$d_6$): $\delta$7.90–7.95 (4H, m), 7.68 (1H, d, J=8.3 Hz), 7.46–7.59 (7H, m), 7.34 (1H, t, J=7.3 Hz), 3.15 (3H, s).

EXAMPLE 2

3-(4-(Methanesulfonyl)phenyl)-2-phenylbenzo[b]thiophene

Step 1: 2-phenylthio-1-(4-(methanesulfonyl)phenyl)ethanone

To a solution of thiophenol (5.5 g) and 2-bromo-1-(4-(methanesulfonyl)phenyl)ethanone (14.8 g) in acetone (250 mL) was added $K_2CO_3$ (13.8 g). The mixture was stirred at r.t. for 1 hr then $H_2O$ added and the solution was extracted with EtOAc, the organic layer was washed with brine, dried over $MgSO_4$, filtered and the solvent evaporated under vacuum. The residue was triturated in EtOAc/$Et_2O$, filtered and air dried, giving 13.4 g of the title compound.

Step 2: 3-(4-(Methanesulfonyl)phenyl)benzo[b]thiophene 2-phenylthio-1-(4-(methanesulfonyl)phenyl)ethanone (1 g) from Step 1 was mixed with PPA (10 g) and heated at 80° C. for 30 minutes. The mixture was then cooled in an ice-water bath and ice was added. The aqueous was extracted twice with EtOAc. The organic layers were combined, washed with brine, dried over $MgSO_4$, filtered and the solvent evaporated in vacuo. Purification by silica gel chromatography using 30% EtOAc in hexane afforded 150 mg of the title compound.

Step 3: 2-Bromo-3-(4-(methanesulfonyl)phenyl)benzo[b]thiophene

To a solution of 3-(4-(methanesulfonyl)phenyl)benzo[b]-thiophene (1 g) from Step 2 in $CH_2Cl_2$ (70 mL) one equivalent of a 1M $Br_2$ solution in $CCl_4$ was added. The mixture was stirred at 25° C. for 2 hrs, then a 10% $Na_2S_2O_3$ solution was added. After extraction with EtOAc, the organic layers were washed with a saturated solution of $NaHCO_3$ (3×), brine, and dried over $MgSO_4$, filtered and the solvent evaporated under vacuum. Purification by column chromatography using 5% EtOAc in toluene afforded the title compound.

Step 4: 3-(4-(Methanesulfonyl)phenyl)-2-phenylbenzo[b]thiophene

A mixture of 2-bromo-3-(4-(methanesulfonyl)phenyl)benzo-[b]thiophene (400 mg) from Step 3, phenylboric acid (590 mg), Pd $(PPh_3)_4$ (89 mg) and 1 molar NaOH in toluene (6 mL) and EtOH (8 mL) was refluxed for 24 hrs. After cooling to 25° C. a saturated $NaHCO_3$ solution was added and the mixture was extracted with $Et_2O$ (2×), the organic portions were combined, washed with brine, dried over $MgSO_4$, filtered and the solvent evaporated under vacuum. Purification by column chromatography using 2% isopropanol in hexane afforded the title compound. m.p. 172.9–173.9° C.

$^1$H NMR δ(ppm) 3.19 (s, 3H), 7.35 (s, 5H), 7.42–7.48 (m, 2H), 7.58–7.64 (m, 3H), 8.02–8.06 (m, 3H).

EXAMPLE 3

3-(4-(Methylsulfonyl)phenyl)-2-phenylinden-1-one

Step 1: 3-(4-(Methylthio)phenyl)-2-phenylinden-1-one

To a solution of p-bromothioanisole (2.04 g, 10 mmol) in THF (40 mL) cooled to −78° C. was added a solution of n-butyl lithium in hexane (4.0 mL of 2.5 M, 10 mmol). The resulting suspension was stirred at this temperature for 20 min. Then a solution of benzalphthalide (2.11 g, 9.5 mmol) in benzene (20 mL) was added and the reaction was allowed to proceed at r.t. for 2 hrs. The reaction turned deep-red. The reaction was completed by addition of conc. $H_2SO_4$ (0.63 mL, 20 mmol) and stirred at r.t. for another 30 min. The reaction was then diluted with EtOAc and a 1:1 mixture of $H_2O$ and saturated aqueous $NaHCO_3$ and extracted. The aqueous layer was extracted one more time with EtOAc. The combined organic extracts were dried over $MgSO_4$ and concentrated to dryness. The crude product was purified by flash chromatography eluted with 10–15% EtOAc in hexane to give the title compound as an orange-red gum.

$^1$H NMR (400 MHz, $CD_3COCD_3$) δ2.55 (3H, s), 7.2–7.4 (11H, m), 7.45–7.55 (2H, m).

Step 2: 3-(4-(Methanesulfonyl)phenyl)-2-phenylinden-1-one

To an ice cold solution of the compound from Step 1 (525 mg, 1.6 mmol) in $CH_2Cl_2$ (16 mL) and MeOH (1.6 mL) was added MMPP (1.09 g, tech. 80%, 1.76 mmol). The resulting suspension was stirred at r.t. for 3 hrs. The reaction was diluted with EtOAc and a 1:1 mixture of $H_2O$ and saturated aqueous $NaHCO_3$ and extracted. The aqueous layer was extracted one more time with EtOAc. The combined organic extracts were dried over $MgSO_4$ and concentrated to dryness. The crude product was purified first by flash chromatography, eluted with EtOAc in hexane 35%, and then crystallized from EtOAc/Hexane (1:1, 20 mL) to give the title compound as a bright orange solid. m.p. 167–168° C.

Mass spectrum: C.I. ($CH_4$) 361 (M+1) $^1$H NMR (400 MHz, $CD_3COCD_3$) δ3.18 (3H, s), 7.18 (1H, d), 7.23–7.32 (5H, m), 7.43 (1H, t), 7.53 (1H, t), 7.59 (1H, d), 7.72 (2H, d), 8.08 (2H, d).

EXAMPLE 4

2-(4-Fluorophenyl)-3-(4-(methylsulfonyl)phenylindole

Step 1: 1-(4-Fluorophenyl)-2-(4-(methylthio)phenyl)ethanone

To 4-fluorobenzaldehyde (5.40 g) in 1,2-dichloroethane (43.50 mL) were added TMS-CN (4.32 g) and $ZnI_2$ (44 mg). After 0.5 h at r.t., the solvent was removed in vacuo. To the resulting TMS cyanohydrin (9.20 g) in THF (42.0 mL) at −78° C. was added dropwise a solution of LDA 0.51M in THF (88.9 mL). After a period of 0.5 h, a THF solution (30.0 mL) of 4-(chloromethyl)thioanisole (9.93 g) was added dropwise over 0.5 h. After 18 h at +5° C., the resulting mixture was treated with 1N tetra-n-butylammonium fluoride in THF (57.5 mL) followed by a 25% aqueous solution of $NH_4OAc$ (100 mL) and extracted with EtOAc (2×150 mL). After evaporation, a 10:1 mixture of $Et_2O$ and hexane (200 mL) was added to the crude ketone. After stirring for 10 h and the title product was obtained as a solid by filtration (2.40 g).

Step 2: 1-(4-Fluorophenyl)-2-(4-(methylsulfonyl)phenyl)ethanone

To 1-(4-Fluorophenyl)-2-(4-(methylthio)phenyl)ethanone of Step 1 (17.9 g) in a solution of $CH_2Cl_2$-MeOH (272.0 mL/27.0 mL) at 0° C. was added MPPM (28.0 g). The cooling bath was then removed and the reaction mixture stirred at r.t. for 1 h. At 0° C., additional MPPM (28.0 g) was added and the reaction mixture kept for 1.5 h at r.t. The insoluble material was filtered followed by evaporation of the solvents; the residue was then extracted with $CH_2Cl_2$—$NaHCO_3$. After evaporation in vacuo, the resulting solid was washed with ether-hexane (1:1) and filtered to provide the title compound (16.8 g).

$^1$H NMR ($CD_3COCD_3$) δ 3.13 (3H, s), 3.58 (2H, s), 7.29 (2H, t), 7.55 (2H, d), 7.88 (2H,d), 8.2 (2H, dd).

Step 3: 2-(4-Fluorophenyl)-3-(4-(methylsulfonyl)phenyl)indole

A solution of phenylhydrazine (203 uL, 1.73 mmol) and 1-(4-fluorophenyl)-2-(4-(methylsulfonyl)phenyl)ethanone (510 mg, 1.73 mmol) (Step 2) in a mixture of toluene/HOAc (2:1; 5 mL) containing 1 drop of methanesulfonic acid was stirred at r.t. overnight. The reaction mixture was diluted with EtOAc and was washed successively with $H_2O$, 1M NaOH, $H_2O$ and dried. Evaporation of the solvent gave a residue which was purified by silica gel chromatography using EtOAc/hexane (1:3+10% $CH_2Cl_2$) as eluent to afford 339 mg of the title compound.

$^1$H NMR $(CD_3)_2CO$: δ 3.15 (3H, s); δ 7.1–7.15 (3H, m); δ 7.45–7.70 (5H, m); 7.9–8.05 (5H, m).

EXAMPLE 5

3-(4-Fluorophenyl)-2-(4-(methylsulfonyl)phenyl) indole

To phenylhydrazine (50 uL) in toluene-HOAc (2:1, 2 mL) was added 2-(4-fluorophenyl)-1-(4-(methylsulfonyl)phenyl) ethanone (105 mg) (prepared from 4-(methylthio) benzaldehyde and 4-fluorobenzyl chloride by the same method as described in Step 1 of Example 4). After 1 hr at 85° C., the reaction mixture was extracted with EtOAc and HCl. After drying over $NaSO_4$ and evaporation in vacuo the title compound was purified by flash chromatography (67 mg).

$^1$H NMR $(CD_3COCD_3)$: δ 3.12 (3H, m), 7.10 (1H, t), 7.25 (3H, m), 7.45 (2H, m), 7.52 (2H, m), 7.20 (2H, m), 7.95 (2H, m), 10.50 (1H, brs). Anal. calcd. for $C_{21}H_{16}FNO_2S$ C, 69.04; H, 4.38; N, 3.84. Found C, 68.66; H, 4.44; N, 3.72.

EXAMPLE 6

2-(4-Fluorophenyl)-3-(4-(methylsulfonyl)phenyl)-4H-thieno[2,3-c]-furan-6-one

Step 1: cis,trans-3-Chloro-3-(4-fluorophenyl)-2-(4-(methylthio)-phenyl)propenal

To a solution of 1-(4-fluorophenyl)-2-(4-(methylthio)-phenyl ethanone from Example 4, Step 1 (2.50 g) in 1,2-dichloroethane (27.0 mL) were introduced the Vilsmeier reagent (Aldrich catalog, 1992–1993) 3.3M (11.6 mL) and DMAP (1.17 g). After a period of 4 h at 80° C., the reaction mixture was extracted with EtOAc and 25% aqueous solution of $NH_4OAc$. After evaporation in vacuo and drying for a few hours, the title product so obtained was used as such for the next step.

Step 2: cis,trans-4-Chloro-4-(4-fluorophenyl)-3-(4-(methylthio)-phenyl)-3-buten-2-ol To a solution of cis,trans-3-chloro-3-(4-fluorophenyl)-2-(4-(methylthio)phenyl) propenal from Step 1 (306 mg) in 10 ml of THF was added 1M solution of MeMgBr in THF (2.4 ml) at −20° C. The reaction mixture was allowed to warm to room temperature over a period of 30 min, and then quenched with 20 ml of sat. $NH_4Cl$. The product was extracted with 50 ml of 2:1 EtOAc/hexane, and the extract was dried over $Na_2SO_4$ and concentrated in vacuo to yield 320 mg of the title compound.

Step 3: cis,trans-4-Chloro-4-(4-fluorophenyl)-3-(4-(methylthio)-phenyl)-3-buten-2-one To a solution of the product of Step 2 (200 mg) in 10 mL of $CH_2Cl2$ were added 0.5 g of powered 4 Å molecular sieve and 0.47 g of PDC. The mixture was stirred for 2 h, diluted with 15 mL of $Et_2O$, and then filtered through a pad of celite. The filtrate was concentrated in vacuo to give 180 mg of the crude title compound which was used for the next step without further purification.

Step 4: cis,trans-4-Chloro-4-(4-fluorophenyl)-3-(4-(methylsulfonyl)phenyl)-3-buten-2-one The crude product of Step 3 (180 mg) was dissolved in 10 mL of 10:1 $CH_2Cl_2/MeOH$ and treated with 250 mg of MPPM. After stirring for 30 min, the reaction mixture was quenched with 20 mL of sat. $NaHCO_3$, and extracted with 50 ml of EtOAc. The extract was dried over $Na_2SO_4$ and concentrated in vacuo to give 150 mg of the title compound.

Step 5: 3-Methyl-5-(4-fluorophenyl)-4-(4-(methylsulfonyl)-phenyl)thiophene-2-carboxylic acid methyl ester To a solution of the product of Step 4 (110 mg) and methyl thioglycolate (42 uL) in 5 ml of $CH_3CN$ was added 50 uL of DBU. After stirring for 20 min, the reaction was quenched with 5 ml of sat. $NH_4Cl$ and 0.5 mL of 1N HCl. The mixture was then extracted with 40 mL of 2:1 EtOAc/hexane. The extract was dried over $MgSO_4$ and concentrated in vacuo. The residue was purified by flash chromatography eluted with 2:1 hexane/EtOAc to provide 100 mg of the title compound.

Step 6: 3-Bromomethyl-5-(4-fluorophenyl)-4-(4-(methylsulfonyl)-phenyl)thiophene-2-carboxylic acid methyl ester A solution of 404 mg of the product of Step 5, 200 mg of NBS, and 5 mg of benzoylperoxde in 10 mL of $CCl_4$ was heated in a 80° C. oil bath under light from a W-lamp. After 30 min, the reaction mixture was cooled to room temperature, diluted with 10 mL of 3:1 EtOAc/hexane, and filtered through a pad of silica gel. The filtrate was concentrated in vacuo to give 400 mg of the crude title compound which was used for the next step without further purification.

Step 7: 3-Hydroxymethyl-5-(4-fluorophenyl)$_4$-(4-(methylsulfonyl)phenyl)thiophene-2-carboxylic acid A mixture of 400 mg of the product of Step 6, 10 g of $n-Bu_4NOAcin$ 10 mL of THF were stirred at room temperature for 2 h. The reaction mixture was diluted with 50 mL of 3:2 $THF/H_2O$ and treated with 10 mL of 1N LiOH for 8 h. The reaction mixture was poured into a mixture of 20 mL of sat. NaCl and 10 mL of 2N HCl, and then extracted with 100 mL of EtOAc. The extract was dried over $MgSO_4$ and concentrated in vacuo. The crude product was purified by flash chromatography and eluted with 19:1 EtOAc/AcOH to yield 250 mg of the title compound.

Step 8: 2-(4-Fluorophenyl)-3-(4-(methylsulfonyl)phenyl)-4H-thieno[2,3-c]furan-6-one To a solution of 110 mg of the product of Step 7 in 15 mL of $CH_2Cl_2$ was added 110 mg of 1-(3-dimethylamninopropyl)-3-ethyl-carbodiimide hydrochloride. After stirring for 20 min, the reaction was quenched with 20 mL of sat. $NaHCO_3$ and extracted with 50 mL of EtOAc. The extract was dried over $MgSO_4$ and concentrated in vacuo. The crude product was suspended in 10 mL of 2:1 EtOAc/hexane with vigorously stirring for 2 h, and filtered to provide 75 mg of the title product as a white solid.

$^1$H NMR $(CD_3COCD_3)$: δ 3.15 (3H, s), 5.47 (2H, s), 7.22 (2H, t), 7.46 (2H, t), 7,60 (2H, d), 7,95 (2H, d).

EXAMPLE 7

2-(3,4-Difluorophenyl)-3-(4-(methylsulfonyl) phenyl)-4H-thieno[2,3-c]-furan-6-one Following the procedure of Example 6, but replacing 1-(4-fluorophenyl)-2-(4-(methylthio)phenyl)ethanone by 1-(3,4-difluorophenyl)-2-(4-(methylthio)phenyl)ethanone, the title compound was prepared. The starting ketone was prepared according to Example 4, step 1, beginning with 3,4-difluorobenzaldehyde.

$^1$H NMR $(CD_3COCD_3)$: δ 3.15 (3H, s), 5.48 (2H, s), 7.26–7.32 (1H, m), 7.38–7.44 (2H, m), 7.63 (2H, d), 7.88 (2H, d).

EXAMPLE 8

2-(4-Fluorophenyl)-3-(4-(aminosulfonyl)phenyl)-4H-thieno[2,3-c]furan-6-one

Step 1: 3-Methyl-5-(4-fluorophenyl)-4-(4-(methylthiophenyl)-thiophene-2-carboxylic acid methyl ester To a solution of cis,trans-4-chloro-4-(4-fluorophenyl)-3-(4-(methylthio)phenyl)-3-buten-2-one (13.8 g) (Example 6, Step 3) and methyl thioglycolate (5.8 mL) in 350 mL of $CH_3CN$ was added 8 mL of DBU. After stirring for 5 h, the reaction was quenched with 250 mL of sat. $NH_4Cl$ and 50 mL of 1N HCl. The mixture was then extracted with 800 ml of 2:1 EtOAc/hexane. The extract was dried over $MgSO_4$ and concentrated in vacuo. The residue was purified by flash chromatography eluted with 10:1 hexane/EtOAc to provide 8.58 g of the title compound.

Step 2: 3-Bromomethyl-5-(4-fluorophenyl)-4-(4-(methylthio)phenyl)thiophene-2-carboxylic acid methyl ester A solution of 389 mg of the product of Step 1, 218 mg of NBS, and 16 mg of benzoylperoxde in 20 mL of $CCl_4$ was heated in a 80° C. oil bath under light from a W-lamp. After 30 min, the reaction mixture was cooled to room temperature, and concentrated in vacuo. The residue was purified by silica gel chromatography eluted with 13:1 hexane/EtOAc to give 413 mg of the title compound.

Step 3: 3-Hydroxymethyl-5-(4-fluorophenyl)-4-(4-(methylthio)-phenyl)thiophene-2-carboxylic acid To a solution of 249 mg of the product of Step 2 in 5 mL of DMF was added 237 mg of $n-Bu_4NOAc$. The reaction mixture was stirred at r.t. for 15 min. Water (20 mL) was added and the product was extracted with 50 mL of EtOAc. The extract was dried over $MgSO_4$ and concentrated in vacuo. The residue was dissolved in 4 mL of THF and 2 mL of MeOH and treated with 1 ml of 1N LiOH. After 12 h, the reaction mixture was treated with 0.2 ml of HOAc and 10 mL of brine. The product was extracted with 40 mL of EtOAc. The extract was dried over $MgSO_4$ and concentrated in vacuo to provide 120 mg of title compound as a white solid.

Step 4: 2-(4-Fluoropbenyl)-3-(4-(methylthio)phenyl)-4H-thieno[2,3-c]furan-6-one

To a solution of 120 mg of the product of Step 3 in 10 mL of $CH_2Cl_2$ was added 150 mg of 1-(3-dimethylaminopropyl)-3-ethylcarbodiimide hydrochloride. After stirring for 30 min, the reaction mixture was concentrated in vacuo and purified by silica gel chromatography eluted with 6:1 hexane/EtOAc to give 89 mg of the title compound.

Step 5: 2-(4-Fluorophenyl)-3-(4-(methylsulfinyl)phenyl)-4H-thieno[2,3-c]furan-6-one 2-(4-Fluorophenyl)-3-(4-(methylthio)phenyl)-4H-thieno-[2,3-c]furan-6-one (548 mg) (from Step 4) was dissolved in 10 mL of 10:1 $CH_2Cl_2$/-MeOH and treated with 476 mg of MPPM at 0° C. After stirring for 15 min at 0° C. and 1.5 h at room temperature, the reaction mixture was quenched with 20 mL of sat. $NaHCO_3$, and extracted with 50 ml of EtOAc. The extract was dried over $MgSO_4$ and concentrated in vacuo. The residue was purified by silica gel chromatography eluted with EtOAc to give 490 mg of the title compound.

Step 6: 2-(4-Fluorophenyl)-3-(4-(aminosulfonyl)phenyl)-4H-thieno[2,3-c]furan-6-one 2-(4-Fluorophenyl)-3-(4-(methylsulfinyl)phenyl)-4H-thieno[2,3-c]furan-6-one (from Step 5) (0.49 g) was dissolved in TFAA (7.0 mL) and 1,2-dichloroethane (1 mL), and refluxed for 45 min. The solvent was then removed in vacuo and the resulting residue was co-evaporated three times with a $Et_3N$-MeOH solution (1:1) (10 mL) to provide a viscous oil after pumping for a few hours. The oil was dissolved in HOAc (10.0 mL) and treated at +10° C. with $Cl_2$ in HOAc (1.9M) (3.5 mL). After stirring for 12 h, the solvent was removed in vacuo and THF (20.0 ml) was added to the resulting mass of product. After bubbling $NH_3$ through for a few minutes at 0° C., the reaction mixture was stirred for 0.5 h at r.t. Water was introduced and the product was extracted with EtOAc. The extract was dried over $MgSO_4$ and concentrated in vacuo. The crude was purified by flash chromatography and eluted with 2:1 EtOAc/hexane to provide the title product as a white solid (0.19 g).

$^1H$ NMR ($CD_3COCD_3$): δ 5.46 (2H, s), 6.65 (1H, s), 7.20 (2H, t), 7.46 (2H, t), 7.50 (2H, d), 7.89 (2H, d).

EXAMPLE 9

2-(3,4-Difluorophenyl)-3-(4-(aminosulfonyl)phenyl) 4H-thieno-[2,3-c]furan-6-one Following the procedures of Example 8, but replacing cis,trans-4-chloro-4-(4-fluorophenyl)-3-(4-(methylthio) phenyl)-3-buten-2-one by cis,trans-4-chloro-4-(3,4-difluorophenyl)-3-(4-(methylthio)phenyl-3-buten-2-one, the title compound was obtained. The requisite difluoro starting material was prepared in an analogous way to the monofluoro analog.

$^1H$ NMR ($CD_3COCD_3$): δ 5.48 (2H, s), 6.68 ($^1H$, s), 7.30 (1H, m), 7.35–7.46 (3H, m), 7.55 (2H, d), 7.92 (2H, d).

EXAMPLE 10

3-(4-(Methylsulfonyl)phenyl)-2-phenyl-4,7-dihydro-thieno[2,3-c]pyran-5-one

Step 1: 3-Cyanomethyl-4-(4-(methylthio)phenyl)-5-phenyl-thiophene-2-carboxylic acid methyl ester To 3-bromomethyl-4-(4-(methylthio)phenyl)-5-phenyl-thiophene-2-carboxylic acid methyl ester (1 g, prepared by using the same procedure described for 3-bromomethyl-5-(fluorophenyl)-4-(4-(methylthio)phenyl)thiophene-2-carboxylic acid methyl ester of Example 8, Step 2 but substituting benzaldehyde for 4-fluorobenz-aldehyde) in DMSO (25 mL) in an ice bath was added powdered KCN. The mixture was stirred for 15 minutes at R.T., then $H_2O$ was added and the mixture was extracted with $Et_2O$ (2X), the organic layers were combined, washed with brine, dried over $MgSO_4$, filtered and the solvent was evaporated under vacuum. Purification by silica gel chromatography afforded the title compound.

Step 2: [2-Hydroxymethyl-4-(4-(methylthio)phenyl)-5-phenylthiophen-3-yl]acetonitrile To a solution of 3-cyanomethyl-4-(4-(methylthio) phenyl)-5-phenylthiophene-2-carboxylic acid methyl ester (480 mg) (Step 1) in THF (13 mL) was added 55 mg of $LiBH_4$ followed by 50 μL of MeOH; then the mixture was heated at 50° C. for 90 min. After cooling to r.t. a few drops of acetone were slowly added, then a saturated solution of $NH_4Cl$. The mixture was then extracted twice with EtOAc, the organic layers combined, washed with brine, dried over $MgSO_4$, filtered and the solvent evaporated under vacuum. Purification by silica gel chromatography using 30% of EtOAc in hexane afforded the title compound.

Step 3: [2-Hydroxymethyl-4-(4-(methylthio)phenyl)-5-phenylthiophen-3-yl]acetic acid A solution of [2-hydroxymethyl-4-(4-(methylthio) phenyl)-5-phenylthiophen-3-yl]acetonitrile (270 mg) in ethylene glycol (10 mL), 2-methoxyethanol (2 mL) and 8N KOH (3 mL) was heated at 100° C. for 1 hr. After cooling to r.t. the solution was acidified with 1N HCl then extracted twice with EtOAc. The organic layers were combined and washed with brine, dried over magnesium sulfate, filtered and the solvent was evaporated under vacuum affording the title compound.

Step 4: 3-(4-(Methylthio)phenyl)-2-phenyl-4,7-dihydrothieno-[2,3-c]pyran-5-one (±)-10-camphorsulfonic acid (5 mg) was added to a solution of [2-hydroxymethyl-4-(4-methylsulfanylphenyl)-5-phenylthiophen-3-yl]acetic acid (100 mg) (Step 3) in CH$_2$Cl$_2$ (5 mL) and the resulting solution was stirred overnight. The solution was diluted with CH$_2$Cl and washed with a saturated solution of NaHCO$_3$, dried over MgSO$_4$, filtered and the solvent was evaporated under vacuum. Purification by silica gel chromatography using 20% of EtOAc in hexane gave the title compound.

Step 5: 3-(4-(Methylsulfonyl)phenyl)-2-phenyl-4,7-dihydrothieno[2,3-c]pyran-5-one A solution of 3-(4-(methylthio)phenyl)-2-phenyl-4,7-dihydrothieno[2,3-c]pyran-5-one (100 mg) and MPPM, (166 mg) in CH$_2$Cl$_2$ (5 mL) and MeOH (1 mL) was stirred overnight. A solution of saturated NaHCO$_3$ was added to the reaction mixture which was extracted with EtOAc. The extract was washed with brine, dried over MgSO$_4$, filtered and the solvent was evaporated under vacuum. Purification by silica gel chromatography using 50% EtOAc in hexane afforded the title compound.

$^1$H NMR (CD$_3$COCD$_3$): δ 3.15 (3H, s), 3,63 (2H, s), 5.66 (2H, s), 7.24 (2H, m), 7.30 (3H, m), 7.51 (2H, d), 7.96 (2H, d).

EXAMPLE 11

2-(4-(Methylsulfonyl)phenyl)-3-phenyl-4H-thieno[2,3-c]-furan-6-one

Step 1: 1-(4-(methylthio)phenyl)-2-phenylethanone

The title compound was prepared from 4-(methylthio)-benzaldehyde and benzyl chloride by the same method as described in Step 1 of Example 4.

$^1$H NMR (CDCl$_3$): δ 7.9 (2H, d), 7.1–7.3 (7H, m), 4.2 (2H, s), 2.5 (3H, s).

Step 2: 2-(4-(Methylthio)phenyl)-3-phenyl-4H-thieno[2,3-c]furan-6-one

The title compound was prepared from 1-(4-(methylthio)-phenyl)-2-phenylethanone by the procedures described in Steps 1, 2, 3, 5, 6, 7 and 8 of Example 6.

$^1$H NMR (CDCl$_3$): δ 7.1–7.4 (9H, m), 5.2 (2H, s), 2.5 (3H, s).

Step 3: 2-(4-(Methylsulfonyl)phenyl)-3-phenyl-4H-thieno[2,3-c]-furan-6-one

The title compound was prepared from 2-(4-(methylthio)-phenyl)-3-phenyl-4H-thieno[2,3-c]furan-6-one by the procedure described in Step 5 of Example 1.

$^1$H NMR (CDCl$_3$): δ 7.86 (2H, d), 7.50 (2H, d), 7.48 (3H, m), 7.14 (2H, m), 5.23 (2H, s), 3.05 (3H, s).

What is claimed is:
1. A compound of Formula

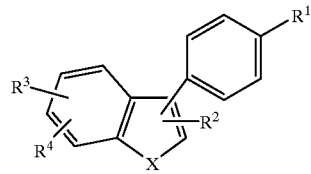

or a pharmaceutically acceptable salt thereof wherein:
X is O or S;
R$^1$ is selected from the group consisting of
(a) S(O)$_2$CH$_3$,
(b) S(O)$_2$NH$_2$,
(c) S(O)$_2$NHCOCF$_3$,
(d) S(O)(NH)CH$_3$,
(e) S(O)(NH)NH$_2$,
(f) S(O)(NH)NHCOCF$_3$,
(g) P(O)(CH$_3$)OH, and
(h) P(O)(CH$_3$)NH$_2$,
R$^2$ is selected from the group consisting of
(a) C$_{1-6}$alkyl,
(b) C$_{3-7}$, cycloalkyl,
(c) mono- or di-substituted phenyl or naphthyl wherein the substituent is selected from the group consisting of
(1) hydrogen,
(2) halo, including F, Cl, Br, I,
(3) C$_{1-6}$alkoxy,
(4) C$_{1-6}$alkylthio,
(5) CN,
(6) CF$_3$,
(7) C$_{1-6}$alkyl,
(8) N$_3$,
(9) —CO$_2$H,
(10) —CO$_2$—C$_{1-4}$alkyl,
(11) —C(R$^5$)(R$^6$)—OH,
(12) —C(R$^5$)(R$^6$)—O—C$_{1-4}$alkyl, and
(13) —C$_{1-6}$alkyl-CO$_2$-R$^7$;
(d) mono- or di-substituted heteroaryl wherein the heteroaryl is a monocyclic aromatic ring of 5 atoms, said ring having one hetero atom which is S, O, or N, and optionally 1, 2, or 3 additional N atoms; or
the heteroaryl is a monocyclic ring of 6 atoms, said ring having one hetero atom which is N, and optionally 1, 2, 3, or 4 additional N atoms; said substituents are selected from the group consisting of
(1) hydrogen,
(2) fluoro, chloro, bromo and iodo,
(3) C$_{1-6}$alkyl,
(4) C$_{1-6}$alkoxy,
(5) C$_{1-6}$alkylthio,
(6) CN,
(7) CF$_3$,
(8) N$_3$,
(9) —C(R$^5$)(R$^6$)—OH, and
(10) —C(R$^5$)(R$^6$)—O—C$_{1-4}$alkyl;
(e) benzoheteroaryl which includes the benzo fused analogs of (d);
R$^3$ and R$^4$ are independently selected from the group consisting of:
(a) hydrogen,
(b) CF$_3$,
(c) CN, (d) $C_{1-6}$alkyl,
(e) —$Q^1$ wherein $Q^1$ is $Q^2$, $CO_2H$, $C(R^5)(R^6)OH$,
(f) —O—$Q^2$,
(g) —S—$Q^2$, and
(h) optionally substituted
  (1) —$C_{1-5}$alkyl-$Q^1$,
  (2) —O—$C_{1-5}$alkyl-$Q^1$,
  (3) —S—$C_{1-5}$alkyl-$Q^1$,
  (4) —$C_{1-3}$alkyl-O—$C_{1-3}$alkyl-$Q^1$,
  (5) —$C_{1-3}$alkyl-S—$C_{1-3}$alkyl-$Q^1$,
  (6) —$C_{1-5}$alkyl-O—$Q^2$,
  (7) —$C_{1-5}$alkyl-S—$Q^2$,
    wherein the substituent resides on the alkyl chain and the substituent is $C_{1-3}$alkyl, and $Q^1$ is $Q^2$, $CO_2H$, $C(R^5)(R^6)OH$ $Q^2$ is $CO_2$—$C_{1-4}$alkyl, tetrazolyl-5-yl, or $C(R^5)(R^6)O$—$C_{1-4}$alkyl;
$R^5$, $R^6$ and $R^7$ are each independently selected from the group consisting of
  (a) hydrogen,
  (b) $C_{1-6}$alkyl,
  or $R^5$ and $R^6$ together with the carbon to which they are attached form a saturated monocyclic carbon ring of 3, 4, 5, 6 or 7 atoms.

2. A compound according to claim 1 wherein
$R^1$ is selected from the group consisting of
  (a) $S(O)_2CH_3$,
  (b) $S(O)_2NH_2$,
  (c) $S(O)_2NHC(O)CF_3$,
  (d) $S(O)NHCH_3$,
  (e) $S(O)NHNH_2$, and
  (f) $S(O)NHNHC(O)CF_3$;
$R^2$ is selected from the group consisting of
  (a) $C_{1-4}$alkyl,
  (b) $C_3$, $C_4$, $C_5$ and $C_6$ cycloalkyl,
  (c) mono- or di-substituted phenyl or naphthyl wherein the substituent is selected from the group consisting of
    (1) hydrogen,
    (2) fluoro, chloro, and bromo,
    (3) $C_{1-4}$alkoxy,
    (4) $C_{1-4}$alkylthio,
    (5) CN,
    (6) $CF_3$,
    (7) $C_{1-4}$alkyl,
    (8) $N_3$,
    (9) —$CO_2H$,
    (10) —$CO_2$—$C_{1-3}$alkyl,
    (11) —$C(R^5)(R^6)$—OH, and
    (12) —$C(R^5)(R^6)$—O—$C_{1-3}$alkyl,
  (d) mono- or di-substituted heteroaryl selected from the group consisting of
    (1) furanyl,
    (2) diazinyl, triazinyl and tetrazinyl,
    (3) imidazolyl,
    (4) isooxazolyl,
    (5) isothiazolyl,
    (6) oxadiazolyl,
    (7) oxazolyl,
    (8) pyrazolyl,
    (9) pyrrolyl,
    (10) thiadiazolyl,
    (11) thiazolyl,
    (12) thienyl,
    (13) triazolyl, and
    (14) tetrazolyl,
wherein said substituents are selected from the group consisting of
  (a) hydrogen,
  (b) fluoro, chloro, bromo,
  (c) $C_{1-4}$alkoxy,
  (d) $C_{1-4}$alkylthio,
  (e) CN,
  (f) $CF_3$,
  (g) $C_{1-4}$alkyl,
  (h) $N_3$,
  (i) —$C(R^5)(R^6)$—OH,
  (j) —$C(R^5)(R^6)$—O—$C_{1-3}$alkyl;
$R^5$ and $R^6$ are each hydrogen or $C_{1-3}$alkyl.

3. A compound according to claim 2 wherein $R^2$ is selected from the group consisting of
  (a) cyclohexyl, and
  (b) mono- or di-substituted phenyl, and wherein the substituents are selected from the group consisting of
    (1) hydrogen,
    (2) halo,
    (3) $C_{1-3}$alkoxy,
    (4) $C_{1-3}$alkylthio,
    (5) CN,
    (6) $CF_3$,
    (7) $C_{1-3}$alkyl,
    (8) $N_3$, and
    (9) —$C(R^5)(R^6)$—OH;
$R^3$ and $R^4$ are each independently selected from the group consisting of
  (a) hydrogen,
  (b) $CF_3$,
  (c) $C_{1-3}$alkyl and hydroxy $C_{1-3}$alkyl,
  (d) chloro and fluoro; and
  (e) CN.

4. A compound according to claim 3 wherein
$R^1$ is selected from the group consisting of
  (a) $S(O)_2CH_3$,
  (b) $S(O)_2NH_2$,
  (c) $S(O)NHCH_3$, and
  (d) $S(O)NHNH_2$;
$R^2$ is selected from the group consisting of
mono or di-substituted phenyl wherein the substituents are selected from the group consisting of
  (1) hydrogen,
  (2) halo, selected from the group consisting of fluoro, chloro and bromo,
  (3) $C_{1-3}$alkoxy,
  (4) $C_{1-3}$alkylthio,
  (5) CN, and
  (6) $C_{1-3}$alkyl;
$R^3$ and $R^4$ are each selected from the group consisting of
  (a) hydrogen,
  (b) $CF_3$,
  (c) $C_{1-3}$alkyl and hydroxy$C_{1-3}$alkyl.

5. A compound according to claim 4 wherein
$R^1$ is selected from the group consisting of
  (a) $S(O)_2CH_3$,
  (b) $S(O)_2NH_2$,
  (c) $S(O)NHCH_3$, and
  (d) $S(O)NHNH_2$;
$R^2$ is
mono or di-substituted phenyl wherein the substituents are selected from the group consisting of
  (1) hydrogen,
  (2) halo, selected from the group consisting of fluoro, chloro and bromo,
  (3) methoxy, and
  (4) methyl.

6. A compound according to claim 5 wherein
$R^1$ is selected from the group consisting of
(a) $S(O)_2CH_3$, and
(b) $S(O)_2NH_2$,
$R^2$ is
mono or di-substituted phenyl wherein the substituents are selected from the group consisting of
(1) hydrogen,
(2) halo, selected from the group consisting of fluoro, chloro and bromo.

7. A compound according to claim 2 wherein $R^2$ is a mono- or di-substituted heteroaryl wherein heteroaryl is selected from the group consisting of
(1) furanyl,
(2) diazinyl, triazinyl, tetrazinyl,
(3) imidazolyl,
(4) isooxazolyl,
(5) isothiazolyl,
(6) oxadiazolyl,
(7) oxazolyl,
(8) pyrazolyl,
(9) pyrrolyl,
(10) thiadiazolyl,
(11) thiazolyl,
(12) thienyl,
(13) triazolyl, and
(14) tetrazolyl,
wherein the substituents are selected from the group consisting of
(a) hydrogen,
(b) fluoro or chloro,
(c) $C_{1-3}$alkoxy,
(d) $C_{1-3}$alkylthio,
(e) CN,
(5) $CF_3$,
(6) $C_{1-3}$alkyl,
(7) —$C(R^5)(R^6)$—OH;
(8) —$C(R^5)(R^6)$—O—$C_{1-4}$alkyl,
wherein $R^5$ and $R^6$ are each independently hydrogen, methyl or ethyl.

8. A compound according to claim 7 wherein $R^2$ is a mono- or di-substituted heteroaryl wherein heteroaryl is selected from the group consisting of
(1) 2-furanyl,
(2) 3-furanyl,
(3) 2-thienyl,
(4) 3-thienyl,
(5) 3-isoxazolyl,
(6) 4-isoxazolyl,
(7) 5-isoxazolyl,
(8) 3-isothiazolyl,
(9) 4-isothiazolyl,
(10) 5-isothiazolyl,
(11) 2-oxazolyl,
(12) 4-oxazolyl,
(13) 5-oxazolyl,
(14) 2-thiazolyl,
(15) 4-thiazolyl,
(16) 5-thiazolyl,
(17) 1,2,3-thiadiazol-4-yl,
(18) 1,2,3-thiadiazol-5-yl,
(19) 1,2,4-thiadiazol-3-yl,
(20) 1,2,4-thiadiazol-5-yl,
(21) 1,3,4-thiadiazol-2-yl,
(22) 1,2,5-thiadiazol-3-yl,
(23) 1,2,3-oxadiazol-4-yl,
(24) 1,2,3-oxadiazol-5-yl,
(25) 1,2,4-oxadiazol-3-yl,
(26) 1,2,4-oxadiazol-5-yl,
(27) 1,3,4-oxadiazol-2-yl,
(28) 1,2,5-oxadiazol-3-yl,
(29) pyrazol-4-yl,
(30) pyrazol-5-yl,
(31) 1,2,3-triadiazol-4-yl,
(32) 1,2,3-triadiazol-5-yl,
(33) 1,2,4-triadiazol-3-yl,
(34) 1,2,4-triadiazol-5-yl,
(35) 1,2-diazinyl,
(36) 1,3-diazinyl,
(37) 1,4-diazinyl,
(38) 1,2,3,4-tetrazin-5-yl,
(39) 1,2,4,5-tetrazin-4-yl,
(40) 1,3,4,5-tetrazin-2-yl, and
(41) 1,2,3,5-tetrazin-4-yl.

9. A compound according to claim 8 wherein the heteroaryl is selected from the group consisting of
(1) 3-isoxazolyl,
(2) 4-isoxazolyl,
(3) 5-isoxazolyl,
(4) 3-isothiazolyl,
(5) 4-isothiazolyl,
(6) 5-isothiazolyl,
(7) 2-oxazolyl,
(8) 4-oxazolyl,
(9) 5-oxazolyl,
(10) 2-thiazolyl,
(11) 4-thiazolyl,
(12) 5-thiazolyl,
(13) 1,2,3-thiadiazol-4-yl,
(14) 1,2,3-thiadiazol-5-yl,
(15) 1,2,4-thiadiazol-3-yl,
(16) 1,2,4-thiadiazol-5-yl,
(17) 1,3,4-thiadiazol-2-yl,
(18) 1,2,5-thiadiazol-3-yl,
(19) 1,2,3-oxadiazol-4-yl,
(20) 1,2,3-oxadiazol-5-yl,
(21) 1,2,4-oxadiazol-3-yl,
(22) 1,2,4-oxadiazol-5-yl,
(23) 1,3,4-oxadiazol-2-yl,
(24) 1,2,5-oxadiazol-3-yl,
(25) 1,2-diazinyl,
(26) 1,3-diazinyl, and
(27) 1,4-diazinyl.

10. A compound according to claim 9 wherein the heteroaryl is selected from the group consisting of
(1) 3-isothiazolyl,
(2) 4-isothiazolyl,
(3) 5-isothiazolyl, (4) 2-oxazolyl,
(5) 4-oxazolyl,
(6) 5-oxazolyl,
(7) 2-thiazolyl,
(8) 4-thiazolyl,
(9) 5-thiazolyl,
(10) 1,2-diazinyl,
(11) 1,3-diazinyl, and
(12) 1,4-diazinyl, and
   wherein the substitutents are selected from the group consisting of
   (1) hydrogen,
   (2) fluoro or chloro,
   (3) $C_{1-3}$alkoxy,
   (4) $C_{1-3}$alkylthio,
   (5) CN,
   (6) $C_{1-3}$alkyl, and
   (7) —C($R^5$)($R^6$)—OH.

11. A compound according to claim 10 wherein
$R^1$ is selected from the group consisting of
   (a) $S(O)_2CH_3$,
   (b) $S(O)_2NH_2$,
   (c) $S(O)NHCH_3$, and
   (d) $S(O)NHNH_2$, and $R^3$ is selected from the group consisting of
   (a) hydrogen,
   (b) $CF_3$,
   (c) $C_{1-3}$alkyl and hydroxy$C_{1-3}$alkyl,
   (d) CN.

12. A compound according to claim 11 wherein the hetereooaryl is selected from the group consisting of
   (1) 3-isothiazolyl,
   (2) 4-isothiazolyl,
   (3) 5-isothiazolyl,
   (4) 2-oxazolyl,
   (5) 4-oxazolyl,
   (6) 5-oxazolyl,
   (7) 2-thiazolyl,
   (8) 4-thiazolyl,
   (9) 5-thiazolyl,
   (10) 1,2-diazinyl,
   (11) 1,3-diazinyl, and
   (12) 1,4-diazinyl,
   wherein the substituents are selected from the group consisting of
   (1) hydrogen,
   (2) fluoro or chloro,
   (3) methoxy,
   (4) methylthio,
   (5) $CF_3$,
   (6) methyl.

13. A pharmaceutical composition for treating an inflammatory disease susceptible to treatment with an non-steroidal anti-inflammatory agent comprising:
   a non-toxic therapeutically effective amount of a compound according to claim 2 and a pharmaceutically acceptable carrier.

14. A pharcaceutical composition for treating cyclooxygenase mediated diseases advantageously treated by an active comprosing:
   a non-toxic therapeutically effectuve amount of a compound according to claim 2 and a pharmaceutically acceptable carrier.

15. A method of treating an inflammatory disease susceptible to treatment with an non-steroidal anti-flammatory agent comprising:
   administration to a patient in need of such treatment of a non-toxic therapeutically effective amount of a compound according to claim 2 and a pharmaceutically acceptable carrier.

16. A method of treating cyclooxygenase mediated diseases advantageously treated by an active agent that selectively inhibits COX-2 in preference to COX-1 comprising:
   administration to a patient in need of such treatment of a non-toxic therapeutically effective amount of a compound according to claim 2.

17. A compound selected from
   (a) 3-(4-(Methylsulfonyl)phenyl)-2-phenylbenzo[b]furan, and
   (b) 3-(4-(Methylsulfonyl)phenyl)-2-phenylbenzo[b]-thiophene.

* * * * *